(12) United States Patent
Shawcross et al.

(10) Patent No.: US 9,808,539 B2
(45) Date of Patent: Nov. 7, 2017

(54) HYPOOSMOTIC SOLUTIONS FOR LYMPH NODE DETECTION

(71) Applicant: Endomagnetics Ltd., Cambridge (GB)

(72) Inventors: Andrew P. Shawcross, Cambridge (GB); John Gonzalez-Carvajal, Haslemere (GB); Marc Brown, Watford (GB); Rob Turner, Portsmouth (GB)

(73) Assignee: ENDOMAGNETICS LTD., Cambridge (GB)

(*) Notice: Subject to any disclaimer, the term of this patent is extended or adjusted under 35 U.S.C. 154(b) by 164 days.

(21) Appl. No.: 14/202,178

(22) Filed: Mar. 10, 2014

(65) Prior Publication Data

US 2014/0314679 A1 Oct. 23, 2014

Related U.S. Application Data

(60) Provisional application No. 61/775,780, filed on Mar. 11, 2013.

(51) Int. Cl.
| | |
|---|---|
| *A61B 5/055* | (2006.01) |
| *A61K 49/18* | (2006.01) |
| *A61K 41/00* | (2006.01) |
| *A61N 2/00* | (2006.01) |

(52) U.S. Cl.
CPC ...... *A61K 49/1806* (2013.01); *A61K 41/0052* (2013.01); *A61K 49/1863* (2013.01); *A61N 2/002* (2013.01)

(58) Field of Classification Search
CPC ......... A61B 5/062; A61B 5/107; A61B 5/004; A61B 1/00009; A61K 9/14; A61K 9/51; A61K 9/08; A61K 9/10
USPC ................. 424/9.1–9.3, 9.323, 489
See application file for complete search history.

(56) References Cited

U.S. PATENT DOCUMENTS

| | | | |
|---|---|---|---|
| 2,614,164 A | 10/1952 | Huston | |
| 3,445,928 A | 5/1969 | Beynon | |
| 3,449,662 A | 6/1969 | Wood | |
| 4,324,255 A | 4/1982 | Barach et al. | |
| 4,825,162 A | 4/1989 | Roemer et al. | |
| 4,983,912 A | 1/1991 | Roehriein et al. | |
| 5,005,001 A | 4/1991 | Cordery | |
| 5,184,070 A | 2/1993 | Besendorfer et al. | |
| 5,261,403 A | 11/1993 | Saito et al. | |
| 5,293,119 A | 3/1994 | Podney | |
| 5,363,845 A | 11/1994 | Chowdhury et al. | |
| 5,368,840 A * | 11/1994 | Unger .................... | A61K 49/08 424/9.35 |
| 5,402,094 A | 3/1995 | Enge | |
| 5,414,356 A | 5/1995 | Yoshimura et al. | |
| 5,416,413 A | 5/1995 | Leussler | |
| 5,437,280 A | 8/1995 | Hussman | |
| 5,492,814 A * | 2/1996 | Weissleder ................... | 435/7.25 |
| 5,512,821 A | 4/1996 | Ando et al. | |
| 5,534,241 A * | 7/1996 | Torchilin ........... | A61K 49/1812 424/450 |
| 5,534,778 A | 7/1996 | Loos et al. | |
| 5,537,037 A | 7/1996 | Otaka et al. | |
| 5,657,756 A | 8/1997 | Vrba et al. | |
| 5,666,052 A | 9/1997 | Sata | |
| 5,844,140 A | 12/1998 | Seale | |
| 5,942,209 A | 8/1999 | Leavitt et al. | |
| 5,997,473 A | 12/1999 | Taniguchi et al. | |
| 6,076,008 A | 6/2000 | Bucholz | |
| 6,082,366 A | 7/2000 | Andrä et al. | |
| 6,123,920 A * | 9/2000 | Gunther ............... | A61K 49/049 424/9.322 |
| 6,173,715 B1 | 1/2001 | Sinanan et al. | |
| 6,205,352 B1 | 3/2001 | Carroll | |
| 6,230,038 B1 | 5/2001 | von Gutfeld et al. | |
| 6,270,464 B1 | 8/2001 | Fulton, III et al. | |
| 6,304,075 B1 | 10/2001 | Schaewen et al. | |
| 6,347,241 B2 | 2/2002 | Burbank et al. | |
| 6,356,782 B1 | 3/2002 | Sirimanne et al. | |
| 6,371,904 B1 | 4/2002 | Sirimanne et al. | |
| 6,394,965 B1 | 5/2002 | Klein | |
| 6,406,420 B1 | 6/2002 | McCarthy et al. | |
| 6,418,335 B2 | 7/2002 | Avrin et al. | |
| 6,427,081 B1 | 7/2002 | Burbank et al. | |
| 6,445,185 B1 | 9/2002 | Damadian et al. | |
| 6,549,800 B1 | 4/2003 | Atalar et al. | |

(Continued)

FOREIGN PATENT DOCUMENTS

| | | |
|---|---|---|
| DE | 29724862 | 12/2004 |
| DE | 102007009016 | 8/2008 |

(Continued)

OTHER PUBLICATIONS

Cash, et al., "Breast Cancers: Noninvasive Method of Preoperative Localization with Three-dimensional US and Surface Contour Mapping," Published online before print Sep. 21, 2007, doi: 10.1148/radiol.2452060906, Nov. 2007, Radiology, 245, 556-566 (downloaded on Sep. 28, 2011 from http://radiology.rsna.org/content/245/2/556.full).

Conners, "Diagnostic uses of metal detectors: a review," Int. J. Clin. Pract., Aug. 2005:59(8), pp. 946-949, Blackwell Publishing.

Fagaly, "Squid Detection of Electronic Circuits," IEEE Transactions on Magnetics, vol. 25, No. 2, Mar. 1989, pp. 1216-1218.

Freitas, Jr., "Nanomedicine, Vol. I: Basic Capabilities," www.nanomedicine.com/NMI/8.2.1.2.htm, Landes Bioscience, Georgetown, TX, 1999, 4 pages.

(Continued)

*Primary Examiner* — Micah-Paul Young
(74) *Attorney, Agent, or Firm* — K&L Gates LLP

(57) ABSTRACT

Provided are compositions for rapid detection of lymph nodes. The compositions include magnetic particles, such as iron oxide, and a solute present in an amount that results in a hypoosomotic solution. Methods for detecting lymph nodes also are provided.

14 Claims, 2 Drawing Sheets

(56) References Cited

U.S. PATENT DOCUMENTS

| | | | |
|---|---|---|---|
| 6,592,608 B2 | 7/2003 | Fisher et al. |
| 6,603,308 B2 | 8/2003 | Itozaki et al. |
| 6,638,913 B1 | 10/2003 | Speck et al. |
| 6,662,040 B1 | 12/2003 | Henrichs et al. |
| 6,662,041 B2 | 12/2003 | Burbank et al. |
| 6,699,205 B2 | 3/2004 | Fulton, III et al. |
| 6,725,083 B1 | 4/2004 | Burbank et al. |
| 6,766,186 B1 | 7/2004 | Hoyns et al. |
| 6,815,949 B2 | 11/2004 | Kandori et al. |
| 6,835,572 B1 | 12/2004 | Mountford et al. |
| 6,850,065 B1 | 2/2005 | Fujita et al. |
| 6,862,470 B2 | 3/2005 | Burbank et al. |
| 6,889,073 B2 | 5/2005 | Lampman et al. |
| 6,920,346 B2 | 7/2005 | Kazandjian et al. |
| 6,949,926 B2 | 9/2005 | Murakami et al. |
| 6,963,769 B1 | 11/2005 | Balaban et al. |
| 6,996,433 B2 | 2/2006 | Burbank et al. |
| 7,009,398 B2 | 3/2006 | Hahn et al. |
| 7,044,957 B2 | 5/2006 | Foerster et al. |
| 7,084,631 B2 | 8/2006 | Qu et al. |
| 7,116,094 B2 | 10/2006 | Levin et al. |
| 7,229,417 B2 | 6/2007 | Foerster et al. |
| 7,283,868 B2 | 10/2007 | Ko et al. |
| 7,329,414 B2 | 2/2008 | Fisher et al. |
| 7,335,511 B2 | 2/2008 | Mountford et al. |
| 7,386,338 B2 | 6/2008 | Hoppel et al. |
| 7,412,275 B2 | 8/2008 | Marinelli |
| 7,416,533 B2 | 8/2008 | Gellman et al. |
| 7,479,784 B2 | 1/2009 | Lee |
| 7,525,308 B2 | 4/2009 | Tsukada et al. |
| 7,535,363 B2 | 5/2009 | Gisselberg et al. |
| 7,570,056 B2 | 8/2009 | Nakabayashi et al. |
| 7,625,397 B2 | 12/2009 | Foerster et al. |
| 7,668,582 B2 | 2/2010 | Sirimanne et al. |
| 7,676,256 B2 | 3/2010 | Satragno et al. |
| 7,680,524 B2 | 3/2010 | Ogawa et al. |
| 7,689,267 B2 | 3/2010 | Prince |
| 7,701,209 B1 | 4/2010 | Green |
| 7,702,378 B2 | 4/2010 | Bolan et al. |
| 7,711,407 B2 | 5/2010 | Hughes et al. |
| 7,744,852 B2 | 6/2010 | Chernomorsky et al. |
| 7,783,336 B2 | 8/2010 | Macfarlane et al. |
| 7,792,569 B2 | 9/2010 | Burbank et al. |
| 7,877,133 B2 | 1/2011 | Burbank et al. |
| 7,972,619 B2 | 7/2011 | Fisher |
| 8,050,742 B2 | 11/2011 | Weizman |
| 8,060,183 B2 | 11/2011 | Leopold et al. |
| 8,062,215 B2 | 11/2011 | Voegele et al. |
| 8,064,987 B2 | 11/2011 | Carr, Jr. |
| 8,118,754 B1 | 2/2012 | Flynn et al. |
| 8,137,320 B2 | 3/2012 | Mark et al. |
| 8,174,259 B2 | 5/2012 | Hattersley et al. |
| 8,219,182 B2 | 7/2012 | Burbank et al. |
| 8,277,391 B2 | 10/2012 | Foerster et al. |
| 8,280,486 B2 | 10/2012 | Miller et al. |
| 2001/0011155 A1 | 8/2001 | Rapoport |
| 2001/0012915 A1 | 8/2001 | Avrin et al. |
| 2001/0049481 A1 | 12/2001 | Fulton, III et al. |
| 2002/0019595 A1 | 2/2002 | Osborne et al. |
| 2002/0035324 A1 | 3/2002 | Sirimanne et al. |
| 2002/0161298 A1 | 10/2002 | Burbank et al. |
| 2003/0016010 A1 | 1/2003 | Kandori et al. |
| 2003/0078493 A1 | 4/2003 | Ogawa et al. |
| 2003/0141868 A1 | 7/2003 | Bakharev |
| 2003/0214313 A1 | 11/2003 | Omura et al. |
| 2003/0216632 A1 | 11/2003 | McClure et al. |
| 2004/0109823 A1 | 6/2004 | Kaplan |
| 2004/0162477 A1 | 8/2004 | Okamura et al. |
| 2004/0236213 A1 | 11/2004 | Jones et al. |
| 2004/0249261 A1 | 12/2004 | Torchia et al. |
| 2005/0033157 A1 | 2/2005 | Klein et al. |
| 2005/0059881 A1 | 3/2005 | Balaban et al. |
| 2005/0136002 A1* | 6/2005 | Fossheim ............ A61B 5/01 424/1.11 |
| 2005/0148863 A1 | 7/2005 | Okamura et al. |
| 2006/0074295 A1 | 4/2006 | Kucharczyk et al. |
| 2006/0173283 A1 | 8/2006 | Axelsson et al. |
| 2006/0258933 A1 | 11/2006 | Ellis et al. |
| 2006/0270930 A1 | 11/2006 | Brasile |
| 2006/0293581 A1 | 12/2006 | Plewes et al. |
| 2007/0093726 A1 | 4/2007 | Leopold et al. |
| 2008/0074109 A1 | 3/2008 | Tsukada et al. |
| 2008/0097199 A1 | 4/2008 | Mullen |
| 2008/0146914 A1 | 6/2008 | Polzin et al. |
| 2008/0161848 A1 | 7/2008 | Fisher |
| 2008/0214930 A1 | 9/2008 | Brasile |
| 2008/0228164 A1 | 9/2008 | Nicoson et al. |
| 2008/0275333 A1 | 11/2008 | Fain et al. |
| 2008/0294036 A1 | 11/2008 | Hoi et al. |
| 2009/0024022 A1 | 1/2009 | Azar et al. |
| 2009/0082662 A1 | 3/2009 | Israel |
| 2009/0118611 A1 | 5/2009 | He |
| 2009/0164161 A1 | 6/2009 | Hong et al. |
| 2009/0201016 A1 | 8/2009 | Hattersley et al. |
| 2010/0030149 A1 | 2/2010 | Carr, Jr. |
| 2010/0061937 A1* | 3/2010 | Magnani ............ A61K 49/1896 424/9.36 |
| 2010/0099978 A1 | 4/2010 | Geppert et al. |
| 2010/0125191 A1 | 5/2010 | Sahin |
| 2010/0305430 A1 | 12/2010 | Troesken |
| 2011/0021888 A1 | 1/2011 | Sing et al. |
| 2011/0133730 A1 | 6/2011 | Hattersley |
| 2011/0137154 A1 | 6/2011 | Hattersley et al. |
| 2012/0229130 A1 | 9/2012 | Hattersley et al. |
| 2013/0236530 A1 | 9/2013 | Rosen |

FOREIGN PATENT DOCUMENTS

| | | |
|---|---|---|
| EP | 0126580 | 11/1984 |
| EP | 0595227 | 5/1994 |
| EP | 0663599 | 5/1997 |
| EP | 1249207 | 10/2002 |
| EP | 0966924 | 8/2003 |
| EP | 1284123 | 7/2005 |
| EP | 1062911 | 6/2007 |
| EP | 1491147 | 3/2010 |
| EP | 2267471 | 12/2010 |
| EP | 2339343 | 6/2011 |
| FR | 2689638 | 10/1993 |
| FR | 2770779 | 5/1999 |
| GB | 2109112 | 5/1983 |
| GB | 2425610 | 11/2006 |
| JP | 02-078983 | 3/1990 |
| JP | 02-281170 | 11/1990 |
| JP | 05-251774 | 9/1993 |
| JP | 06-324021 | 11/1994 |
| JP | 08-015229 | 1/1996 |
| JP | 08-248004 | 9/1996 |
| JP | 08-338864 | 12/1996 |
| JP | 09-027057 | 1/1997 |
| JP | 10-038854 | 2/1998 |
| JP | 2003-149212 | 5/2003 |
| JP | 2005-168678 | 6/2005 |
| JP | 2006-030004 | 2/2006 |
| WO | 95/04287 | 2/1995 |
| WO | 98/07052 | 2/1998 |
| WO | 00/38579 | 7/2000 |
| WO | 02/39917 | 5/2002 |
| WO | 2005/011512 | 2/2005 |
| WO | 2006/009048 | 1/2006 |
| WO | 2006/022786 | 3/2006 |
| WO | 2006/056739 | 6/2006 |
| WO | 2006/117530 | 11/2006 |
| WO | 2007/034196 | 3/2007 |
| WO | 2007053533 | 5/2007 |
| WO | 2011033306 | 3/2011 |
| WO | 2011/067576 | 6/2011 |
| WO | 2014/013235 | 1/2014 |

OTHER PUBLICATIONS

Gopee, et al., "Migration of Intradermally Injected Quantum Dots to Sentinel Organs in Mice," Toxicological Sciences, vol. 98(1), Apr. 2007, pp. 249-257.

(56) References Cited

OTHER PUBLICATIONS

Gunasekera, et al., "Imaging applications of nanotechnology in cancer," Targeted Oncology, 2009, vol. 4, pp. 169-181.
Harnan, S.E. et al., "Magnetic resonance for assessment of axillary lymph node status in early breast cancer: A systematic review and meta-analysis," EJSO the Journal of Cancer Surgery, 2011, vol. 37, pp. 928-936.
Jakub et al., "Current Status of Radioactive Seed for Localization of Non Palpable Breast Lesions," The American Journal of Surgery, vol. 199, No. 4, Apr. 2010, pp. 522-528.
Kim, et al., "Near-infrared fluorescent type II quantum dots for sentinel lymph node mapping," Nat Biotechnol., vol. 22(1), Jan. 2004, pp. 93-97.
Meenach, "Synthesis and Characterization of Magnetic Hydrogel Nanocomposites for Cancer Therapy Applications," Doctoral Dissertations, paper 108, 2010, http://uknowledge.uky.edu/gradschool_diss/108.
Noguchi, et al., "Sentinel lymphadenectomy in breast cancer: identification of sentinel lymph node and detection of metastases," Breast Cancer Research and Treatment, vol. 53, 1999, pp. 97-104.
Peleg, et al., "Implementing metal detector technology and a navigation system in the removal of shrapnel," Computer Aided Surgery, Dec. 2009, vol. 14, No. 1-3; pp. 63-68.
Peleg, et al., "Integration of computer-aided navigation and metal detector technology in the removal of shrapnel in terror attacks casualties," 7th Int. Conf. Computer-Aided Orthopaedic Surgery, Heidelberg, Germany, 2007, pp. 57-60.
Postma et al., "Localization of Nonpalpable Breast Lesions," Expert Rev. Anticancer Ther., vol. 11, No. 8, 2011, pp. 1295-1302.
Reddy et al., "Preparation & Application of Magnetic Hydrogel Nanocomposites for Protein Purification and Metal Absorption," International conference on Advances in Polymer Technology, Feb. 26-27, 2010, India, pp. 83-97.
Soltesz, et al., "Intraoperative Sentinel Lymph Node Mapping of the Lung Using Near-Infrared Fluorescent Quantum Dots," Ann Thorac. Surg., vol. 79(1), Jan. 2005, pp. 269-277 (reproduced from NIH Public Access).
Tsay, Tzong T. et al.,"Deep Cervical Lymph Flow Following the Infusion of Mannitol in Rabbits," Life Sciences; 1997, vol. 61; No. 19, pp. 1929-1934.
Williamson, S.J. et al., "Biomagnetism," Journal of Magnetism and Magnetic Materials, XP000574230, 1981, vol. 22; pp. 129-201.
English translation of Office Action for Japanese Patent Application No. 2008-508306, dated Nov. 8, 2011, 6 pages.
European Search Report for EP 10180206, dated Nov. 23, 2010, 4 pages.
Material Safety Data Sheet; Revision Date Mar. 5, 2007; Retrieved from the Internet: URL:https://tools.lifetechnologies.com/content/sfs/msds/2007/11361D VIAL1_MTR-NAIV_EN.pdf [retrieved on Jun. 10, 2014], abstract, (6 pages).
PCT International Search Report and Written Opinion of International Searching Authority for International Patent Application No. PCT/GB2010/002233, dated Mar. 16, 2011, 15 pages.
PCT International Search Report and PCT Written Opinion of International Searching Authority for International Patent Application No. PCT/GB2013/051885, dated Nov. 14, 2013, 18 pages.
PCT International Search Report and the Written Opinion of the International Searching Authority for International Application No. PCT/GB2014/050698, dated Jun. 25, 2014, 14 pages.
PCT International Preliminary Report on Patentability for International Application No. PCT/GB2014/050698, dated Sep. 15, 2015, 9 pages.
PCT International Search Report and the Written Opinion of the International Searching Authority for International Application No. PCT/GB2014/050731, dated Jun. 24, 2014, 15 pages.
PCT International Preliminary Report on Patentability for International Application No. PCT/GB2014/050731, dated Sep. 15, 2015, 10 pages.
PCT Invitation to Pay Additional Fees and Partial International Search Report of the International Searching Authority for International Application No. PCT/GB2014/050732, dated Jun. 26, 2014, 6 pages.
PCT International Preliminary Report on Patentability for International Application No. PCT/GB2014/050732, dated Sep. 15, 2015, 13 pages.

* cited by examiner

HYPOOSMOTIC SOLUTIONS FOR LYMPH NODE DETECTION

RELATED APPLICATIONS

This application claims priority to U.S. Provisional Patent Application 61/775,780 filed Mar. 11, 2013, the entire contents of which is herein incorporated by reference.

FIELD OF THE INVENTION

The invention relates to the field of medical diagnostics in general and diagnostic methods and devices for locating tissue for surgical excision.

BACKGROUND

Approximately 1.25 million new cases of breast cancer are diagnosed each year. In a majority of these cases, there is an urgent need for surgery to remove the tumor and to excise the sentinel lymph nodes and inspect them histologically to determine whether the cancer has spread to other sites in the body. The sentinel lymph nodes are the first nodes to receive lymphatic drainage from the tumor. They are called this because they reliably alert the clinician to any cancer spread. A sentinel lymph node biopsy is a standard of care in breast cancer operations today.

Locating sentinel nodes during surgery is difficult. One method for locating the sentinel node is to inject a dark blue dye into the lymphatic system in the breast. The dye then disperses throughout the breast lymphatic system and the surgeon removes any colored nodes. This method is recognized as being error-prone.

An improved method involves injecting a radioactive dye into the lymph nodes. In a similar manner, the dye drains through the lymphatic system and the surgeon then uses a radiation detector to help locate the sentinel nodes. However, the use of radioisotopes presents a significant, and an expensive, logistical burden, because of the need to allocate the time and resources of a nuclear medicine radiologist in addition to the surgeon for what is otherwise a routine operation. Further, many patients are reluctant to receive a radioactive injection. These factors can become a significant barrier to the use of radioisotopes to locate the sentinel nodes.

A further improved method involved injecting suspensions of magnetic particles into the lymph nodes and waiting for the magnetic particles to drain though the lymphatic system. The particles are then detected using a magnetometer, which reveals the location of the lymph nodes. See US2011/0133730. Prior art solutions, such as Sienna+®, have a very low osmolality of about 30 mOsm/kg. Sienna+® is an aqueous solution of maghemite nanoparticles coated in carboxydextran, having an iron concentration of about 25.5 to 29.5 mg/mL. It takes about 30 minutes for the magnetic particles in a Sienna+® injection to drain sufficiently through the lymphatic system to ensure accurate lymph node detection, which can potentially cause significant and costly downtime during surgical procedures. Consequently, impatient physicians may attempt to detect the lymph nodes too soon—i.e., before the magnetic particles have sufficiently drained through the lymphatic system—which could result in incomplete lymph node detection.

A need therefore exists for compositions that enable more efficient procedures.

The present invention addresses this need.

SUMMARY OF THE INVENTION

The invention relates to a hypoosmotic suspension for medical injection. In one embodiment, the composition includes about 13 mg/mL to about 200 mg/mL of magnetic particles, and an osmolyte from either about 0.01% w/v to about 0.6% w/v of an inorganic salt (e.g., sodium chloride) or about 0.5% w/v to about 1.5% w/v of a glycol.

Embodiments of the hypoosmotic suspensions can include one or more of the following features:

The magnetic particles can be iron oxide particles, such as superparamagetic iron oxide particles (e.g., maghemite).

The magnetic particles can be coated, such as with dextran (e.g. carboxydextran).

The suspensions can have about 13 mg/mL of magnetic particles, about 28 mg/mL of magnetic particles, 56 mg/ml of magnetic particles, 100 mg/ml of magnetic particles, 140 mg/ml of magnetic particles or about 200 mg/mL of magnetic particles.

The suspension can have an osmolality of about 80 mOsm/kg to about 160 mOsm/kg.

The suspension can include an excipient.

The inorganic salt can be present in the amount of about 0.01% w/v-0.6% w/v, about 0.05% w/v-0.3% w/v, about 0.1% w/v-0.3% w/v, less than about 0.6% w/v or about less than about 0.3% w/v.

The invention also provides a method of locating a lymph node in a patient (e.g., a human). The method includes the steps of: providing a hypoosmotic suspension; injecting the hypoosmotic suspension into the patient; waiting until the magnetic particles become entrapped in a lymph node; and detecting the location of the lymph node by detecting the location of the magnetic particles.

The method can include one or more of the following features:

The method can include injecting 0.2 mL of hypoosmotic suspension, 0.4 mL of hypoosmotic suspension, or 0.8 mL of hypoosmotic suspension into the patient.

The detecting can be performed using a magnetometer.

The invention also provides a method of rapidly locating a lymph node in a patient (e.g., a human). The method can include the steps of: providing a hypoosmotic suspension comprising magnetic particles; injecting the hypoosmotic suspension into the patient; and detecting a lymph node within 10 minutes, or within as little as 5 minutes, of injection by detecting the location of the magnetic particles, the detecting sufficient to immediately begin a medical procedure on the lymph node based on the detecting.

The invention also provides a method of treating a patient using magnetic hyperthermia, the method comprising the steps of: providing the hypoosmotic suspension; injecting the hypoosmotic suspension into the patient; and exposing the patient to an alternating magnetic field.

BRIEF DESCRIPTION OF DRAWINGS

The figures are not necessarily to scale, emphasis instead generally being placed upon illustrative principles. The figures are to be considered illustrative in all aspects and are not intended to limit the invention, the scope of which is defined only by the claims.

DETAILED DESCRIPTION

Figure 1:
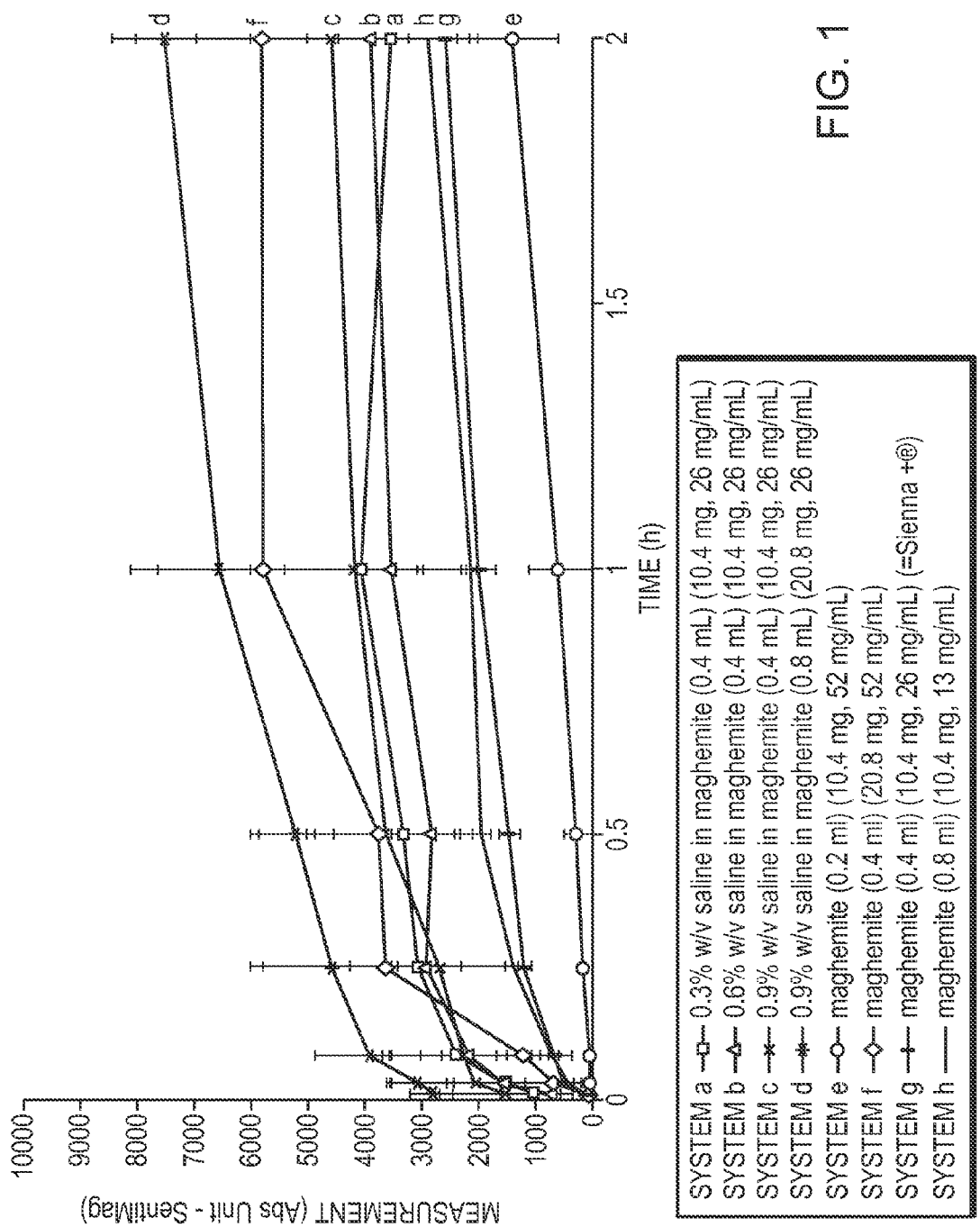
FIG. 1. SentiMag® magnetometer measurements (Abs Unit) at the lymph gland for various salt-based hypoosmotic solutions. Results presented as mean±SEM from 0 to 2 h, n=3.

The invention relates in part to the discovery of compositions useful for rapid detection of lymph nodes in patients. These compositions include suspensions of magnetic particles in a hypoosmotic solution. The osmolality of the hypoosmotic solutions facilitates rapid drainage or transport of the magnetic particles through the lymphatic system after injection, thereby reducing downtime between initial injection and lymph node detection. Lymph nodes adjacent the injection site can be detected robustly in as little as 5 to 15 minutes after initial injection, which is at least 50% faster than current methods, thereby permitting more efficient pre-operative examination. In addition, the hypoosmotic solutions of the invention are versatile solvents and can be used with a wider range of excipients than isotonic or hypertonic solutions. Furthermore, rapid movement to the lymph nodes may reduce residual marking, or tattooing, at the site of injection.

Hypoosmotic solutions within the meaning of the invention are aqueous solutions having an osmolality of about 80 mOsm to about 160 mOsm. Isotonic solutions have an osmolaltiy of around 300 mOsm, and Hyperosmotic solutions have an osmolaltiy of greater than 350 mOsm.

In preferred embodiments, an inorganic salt (e.g., sodium chloride) or a glycol (e.g., propylene glycol) is used to create the hypoosmotic solution. Inorganic salt solutions (e.g., sodium chloride) having about 0.01% w/v to about 0.6% w/v of a salt yield suitable hypoosomotic solutions for use with the invention. Glycol solutions (e.g., propylene glycol) having about 0.5% w/v to about 1.5% w/v of a glycol yield suitable hypoosomotic solutions for use with the invention.

Hypoosmotic solutions can be made using suitable inorganic salts including, for example, monovalent and divalent salts such as sodium chloride, potassium chloride, magnesium chloride, ammonium chloride, sodium bicarbonate, sodium bisulfate, sodium sulfate, ammonium sulfate, sodium phosphate, potassium phosphate, calcium chloride, magnesium sulfate, potassium acetate, and sodium acetate.

Hypoosmotic solutions can be made using suitable glycols including, for example, short chain, linear or branched alkyl glycols, such as propylene glycol.

The magnetic particles can be composed of a suitable magnetic material and one or more coatings. In some embodiments, the magnetic particles contain an iron oxide such as magnetite and/or maghemite. The magnetic core can be surrounded by a biocompatible coating to reduce toxicity, prevent agglomeration of the particles, or to modify residence time in the body. Suitable coatings include, for example, dextran, carboxydextran, other sugars, albumin, polyethylene glycol (PEG), biocompatible polymers, pegylated starch, polyvinyl alcohol (PVA), polyvinylpyrrolidone (PVP), polyethyleneimine (PEI), polyglucose sorbitol carboxymethylether and chitosan. Other coating materials include metals such as gold, pegylated colloidal gold nanoparticles, silver, carbon, silica, silicones, aminosilanes and ceramics. To exhibit superparamagnetic behavior, the magnetic cores of the particles should be below a certain diameter, typically in the range 3-25 nm, depending on the material and structure.

Magnetic particles can also be functionalized to allow them to localize in particular tissue or cell types, for example cancerous cells, or to target particular biological systems in order to deliver therapies to those areas. Functionalization is achieved by attaching or coating with biovectors comprising, for example, antibodies, enzymes or proteins.

In one embodiment, iron oxide is used as the magnetic core because of its low toxicity, but other materials that can form a superparamagnetic core also are acceptable. The core material should be capable of being magnetically ordered. It may be a metal, such as cobalt, iron, or nickel, a metal alloy, rare earth and transition metal alloy, M-type or spinel ferrite containing aluminium, barium, bismuth, cerium, chromium, cobalt, copper, dysprosium, erbium, europium, gadolinium, holmium, iron, lanthanum, lutetium, manganese, molybdenum, neodymium, nickel, niobium, palladium, platinum, praseodymium, promethium, samarium, strontium, terbium, thulium, titanium, vanadium, ytterbium, and yttrium or a mixture thereof. The core can also be formed by oxidising a combination of an iron(II) salt and another metal salt. The metal salts which are beneficial include salts of aluminium, barium, bismuth, cerium, chromium, cobalt, copper, dysprosium, erbium, europium, gadolinium, holmium, iron, lanthanum, lutetium, manganese, molybdenum, neodymium, nickel, niobium, palladium, platinum, praseodymium, promethium, samarium, strontium, terbium, thulium, titanium, vanadium, ytterbium, and yttrium.

The osmolality of the hypoosmotic solutions have the further advantage of permitting combination with a wide range of excipients, resulting in diverse formulation options. Suitable excipients that can be used with the hypoosmotic solutions of the invention include, for example:

co-solvents such as ethanol, propylene glycol, polypropylene glycol, PEG 400, glycerol, benzyl alcohol, and combinations thereof;

oils such as lipids, liquid paraffin, sesame oil, PEG vegetable oil, and combinations thereof surfactants such as polyoxylene fatty acid esters, polyoxyl 40 castor oil, polysorbate 20, polysorbate 80, and combinations thereof;

liposomes such as lecithin, egg lecithin, phosphatidyl glycerol, phospholipid, egg phospholipid, and combinations thereof;

carbohydrates such as dextrose;

amino acids or amino acid mixtures, such as Aminosyn® II, Travasol®, and HepatAmine®;

thickening/stabilizing agents such as carboxymethylcellulose; and buffers suitable for injection.

If an excipient increases the osmolality of a solution, the amount of inorganic salt and/or glycol can be adjusted such that the total osmolality of the hypoosmotic solution is between about 80 mOsm and about 160 mOsm.

The compositions of the invention can be used to detect lymph nodes in humans or any other mammal, such as pigs. For example, a hypoosmotic solution comprising magnetic particles can be injected into a breast cancer patient. Magnetic particles in the solution are then detected using a magnetometer such as SentiMag® (Endomagnetics; Cambridge, U.K.) to reveal the location of the sentinel lymph nodes in the patient.

A further application of the hypoosmotic solution is in magnetic hyperthermia where the solution is administered to the body for the purpose of heating tissue. In this application the concentration of nanoparticles is between 20 and 200 mg/ml and more preferably between 100 and 140 mg/ml.

The hypoosmotic compositions of the invention can be supplied ready-to-use as part of a kit comprising a container, such as vial or syringe, and instructions for administering the compositions.

EXAMPLES

Example 1

Clinical trials with human patients using 2 ml Sienna+® (Endomagnetics; Cambridge, U.K.) was shown to give slow uptake in the axillary lymph nodes, with a poor external signal after 30 minutes. Sienna+® is highly hypotonic, with an osmolality of ~30 mOsm/kg. It was speculated that when Sienna+® was injected into interstitial tissue, the surrounding cells rapidly absorbed water from the injection to maintain osmotic pressure. This would leave a more concentrated mass of Sienna+® while simultaneously reducing interstitial pressure, effectively reducing transport to the lymph system. It is believed that an increase in volume increases interstitial pressure and thereby increases the speed of uptake by the lymphatic system. However, large increases in volume might prove uncomfortable to the patient. In addition, some potential applications for sentinel lymph node biopsy (e.g., bowel, melanoma, some head and neck cancers) will not allow an increase in injection volume. It was hypothesized that an increased osmolality solution would provide a quicker response as the fluid volume and pressure in the interstitial fluid would be maintained (isotonic) or even increased (for hypertonic injection, where surrounding cells would expel water), thus increasing flow to the lymph nodes.

Methods

Pig mammaries were used as an in vivo lymph node model. An investigation was performed to assess the effects of concentration and volume of carboxydextran coated maghemite nanoparticle solution on the bio-distribution of superparamagnetic iron oxide particles in pigs, following an injection of the solution directly into the $3^{rd}$ inguinal papillar. The maghemite core had a diameter of about 5 nm, and the carboxydextran coating increased particle diameter to about 60-70 nm. The aim of this study was to assess the bio-distribution of the superparamagnetic iron oxide particles in pig lymph nodes following injections of the maghemite nanoparticle solution prepared with 0.3, 0.6 and 0.9% w/v sodium chloride. The influence of tonicity upon lymph node bio-distribution of the particles was evaluated through use of a SentiMag® magnetic probe.

Prior to injection, pigs were sedated with an intramuscular combination of azaperone and ketamine, followed by general anesthesia with intravenous sodium thiopental. Before administration, the administration areas were washed and demarked.

All injections were made directly into the base of the 3rd inguinal papilla. Each pig received a different injection in the left papilla and the right papilla. Each of the test solutions was injected into three papilla of different pigs (n=3). Table 1 shows the tested formulations. In Table 1, the "System" column corresponds to the curves in FIG. 1.

TABLE 1

Formulations tested.

| System | Tonicity | Injection Volume | Total iron | Iron Concentration |
|---|---|---|---|---|
| a | 0.3% w/v saline | 0.4 mL | 10.4 mg | 26 mg/mL |
| b | 0.6% w/v saline | 0.4 mL | 10.4 mg | 26 mg/mL |
| c | 0.9% w/v saline | 0.4 mL | 10.4 mg | 26 mg/mL |
| d | 0.9% w/v saline | 0.8 mL | 20.8 mg | 26 mg/mL |
| e | 0 | 0.2 mL | 10.4 mg | 52 mg/mL |
| f | 0 | 0.4 mL | 20.8 mg | 52 mg/mL |
| g | 0 | 0.4 mL (Sienna+ ®, control) | 10.4 mg | 26 mg/mL |
| h | 0 | 0.8 mL | 10.4 mg | 13 mg/mL |

Carboxydextran coated maghemite nanoparticle solutions were prepared in water. NaCl was added to the maghemite solution to the appropriate concentration. For example, a 0.3% salt magnetic particle suspension was created by adding 0.3 mg of NaCl to a prediluted maghemite nanoparticle solution. Sienna+® (~26 mg/mL maghemite, 0.4 mL dose; system g) served as the control.

Multiple readings were taken for each pig using an SentiMag® device, as detailed in Table 2. Following the 72 h readings, the site of papilla and lymph nodes were removed from all animals for histological analysis. The results in FIG. 1 are averages (n=3) of the measurements taken at the lymph nodes.

TABLE 2

SentiMag ® measurement sites and time points.

| Measurement location | Prior to injection | After injection | | | | | | | | | |
|---|---|---|---|---|---|---|---|---|---|---|---|
| | | 30 s | 2 min | 5 min | 15 min | 30 min | 1 h | 2 h | 6 h | 24 h | 72 h |
| Directly on papillar | x | x | x | x | x | x | x | x | x | x | x |
| 2nd inguinal papillar | x | x | x | x | x | x | x | x | x | x | x |
| Lymph node | x | x | x | x | x | x | x | x | x | x | x |

Results

Sienna+® in 0.3% w/v saline solution (FIG. 1, system a) was found to be as efficacious as both the 0.6% and 0.9% saline solutions (FIG. 1, systems b and c, respectively). This was surprising because a 0.3% w/v solution is hypotonic (156 mOsm) compared to 0.6% w/v (270 mOsm—approximately isotonic) and 0.9% w/v (384 mOsm—hypertonic). Such strong results for a 0.3% w/v solution are unexpected. It is believed that the low tonicity will extend the range of formulation additives (excipients) that can be used, as compared to 0.6% and 0.9% solutions.

Specifically, increasing tonicity results in significantly more rapid transport of iron particles through the lymphatic system. At 5 minutes post injection, the addition of 0.3%, 0.6%, and 0.9% salt to Sienna+® (FIG. 1, systems a, b, and c, respectively) result in a five-fold increase in signal measured at the lymph gland as compared to the control, Sienna+® (FIG. 1, system g). As a result, a treating physician need only wait 5-15 minutes before beginning a procedure, which reduces the wait time by at least 50% as compared to Sienna+® alone.

Furthermore, at the 30 minute time point, the impact of adding 0.3%, 0.6%, or 0.9% w/v sodium chloride to Sienna+® (FIG. 1, systems a, b and c, respectively) is equivalent to doubling the concentration of iron (FIG. 1, system f). Consequently, increasing tonicity requires less total iron be used per injection, thereby reducing costs and side effects.

Thus, a hypoosmotic <0.6% NaCl solution and more preferably <0.3% NaCl solution provides the same rapid transport to the lymph nodes as an isotonic (e.g. 0.6% NaCl) or even a hypotonic (e.g. 0.9% NaCl) solution but without requiring such a large amount of salt to be included in the solution.

A more hypotonic solution containing 0.05% w/v NaCl showed no significant improvement over Sienna+®. The "trigger-point" for tonicity benefit is therefore somewhere between about 80 mOsm and about 156 mOsm. Thus, a 0.05% to 0.3% NaCl solution or preferably a 0.1% to 0.3% NaCl solution, or more preferably a 0.2% to 0.3% NaCl solution exhibits both rapid uptake and versatility as an excipient.

Example 2

Similar in vivo pig studies were undertaken to investigate hypoosmotic solutions comprising alternative solutes. All injections were made directly into the base of the 3rd inguinal papilla. Each pig received a different injection in the left papilla and the right papilla. Each test solution was injected into the three papilla of different pigs (n=3). Table 3 shows the tested formulations. In Table 3, the "System" column corresponds to the curves in FIG. 2.

TABLE 3

Solution formulations.

| System | Solution | Tonicity (mOsm/kg) |
|---|---|---|
| 1 | Sienna+ with 0.3% NaCl and 0.1% HA | 132 |
| 3 | Sienna+ with 0.3% NaCl and 1% polysorbate 20 | 135 |
| 5 | Sienna+ with 0.5% propylene glycol | 128 |
| 6 | Sienna+ with 0.3% NaCl (control) | 126 |
| 7 | Sienna+ 0.75% glycerol | 136 |
| 13 | Sienna+ 0.5% propylene glycol and 1.8% glycerol | 297 |

Figure 2:
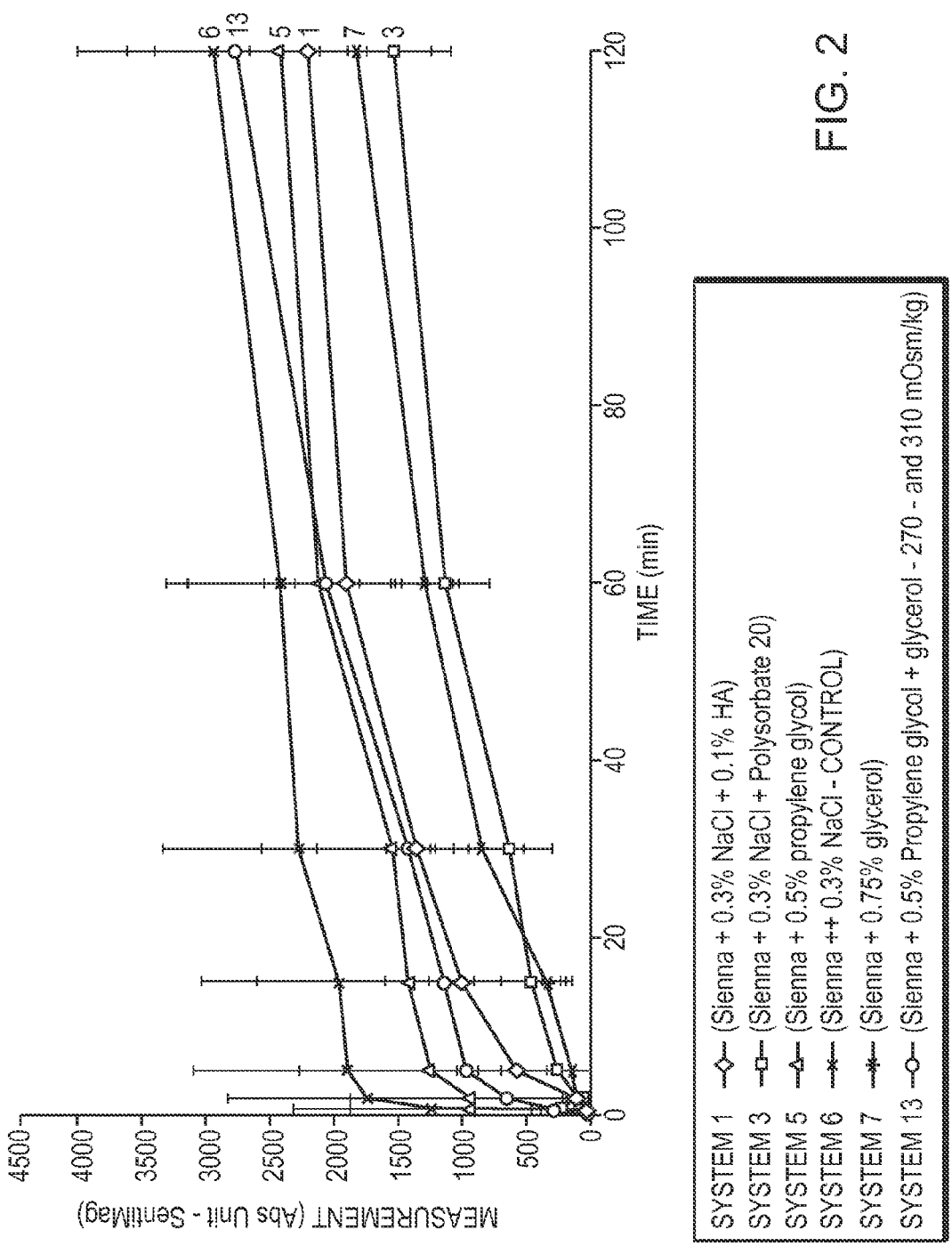
FIG. 2. SentiMag® magnetometer measurements (Abs Unit) at the lymph node for various salt- and non-salt-based hypoosmotic solutions. Results presented as mean±SEM from 0 to 120 min, n=3.

System 6, Sienna+® with 0.3% NaCL served as the control. Multiple readings were taken for each pig using a SentiMag® device, as detailed in Table 4. The results in FIG. 2 are averages (n=3) of the measurements taken at the lymph nodes.

TABLE 4

SentiMag ® measurement sites and time points.

| Measurement location | Prior to injection | After injection | | | | | | | |
|---|---|---|---|---|---|---|---|---|---|
| | | 30 s | 2 min | 5 min | 15 min | 30 min | 1 h | 2 h | 72 h |
| Injection site | x | x | x | x | x | x | x | x | x |
| 2nd inguinal papillar | x | x | x | x | x | x | x | x | x |
| Inguinal lymph node | x | x | x | x | x | x | x | x | x |

As shown in FIG. 2, system 6 (Sienna+0.3% NaCl—CONTROL) resulted in the fastest delivery to the lymph gland. Salt therefore appears to be the best potentiator for delivery. 0.5% polyethylene glycol (system 5) also appears to be efficacious, resulting in rapid delivery to the lymph gland within 5-15 minutes of injection. Accordingly, in some embodiments, glycols can be used as a solute to create a hypoosmotic solution comprising magnetic particles.

The polysorbate (system 3) and glycerol (system 7) formulations were the poorest performing formulations over the first two hours, despite the tonicity being equal to that of the NaCl control (system 6), indicating that polysorbate and glycerol potentially inhibit delivery to the lymph glands. Similarly, addition of hyaluronic acid (MW 108,000 Daltons) appears to retard delivery when combined with 0.3% NaCl.

It should be noted that the method of administration of the solution will depend on the particular site in the body at which it is being administered. For sentinel lymph node biopsy, the injection may be interstitial, sub-cutaneous, intradermal or intramuscular. For magnetic hyperthermia, the solution may be administered by any of these injection methods or via a catheter or infusion into a region of tissue, a body cavity, or vessel.

It should be understood that the order of steps or order for performing certain actions is immaterial, provided that the invention remains operable. Moreover, two or more steps or actions may be conducted simultaneously.

Where a range or list of values is provided, each intervening value between the upper and lower limits of that range or list of values is individually contemplated and is encompassed within the invention as if each value were specifically enumerated herein. In addition, smaller ranges between and including the upper and lower limits of a given range are contemplated and encompassed within the invention. The listing of exemplary values or ranges is not a disclaimer of other values or ranges between and including the upper and lower limits of a given range.

What is claimed is:

1. A hypoosmotic suspension for medical injection comprising:
about 13 mg/mL to about 200 mg/mL of superparamagnetic particles; and an osmolyte selected from either about 0.01% w/v to about 0.6% w/v of an inorganic salt or about 0.5% w/v to about 1.5% w/v of a glycol wherein the hypoosmotic suspension has an osmolality of about 80 mOsm/kg to about 160 mOsm/kg.

2. The hypoosmotic suspension of claim 1, wherein the superparamagnetic particles are iron oxide.

3. The hypoosmotic suspension of claim 1, comprising between about 13 mg/ml and 53 mg/ml of superparamagnetic particles.

4. The hypoosmotic suspension of claim 1, further comprising an excipient.

5. The hypoosmotic suspension of claim 1 wherein the superparamagnetic particles are coated.

6. The hypoosmotic suspension of claim 5, wherein the coating comprises dextran.

7. The hypoosmotic suspension of claim 1, wherein the inorganic salt is sodium chloride.

8. The hypoosmotic suspension of claim 1, wherein the suspension is used for the detection of sentinel nodes and comprises about 0.05%-0.3% w/v of the inorganic salt.

9. The hypoosmotic suspension of claim 1, wherein the glycol is propylene glycol.

10. The hypoosmotic suspension of claim 1, wherein the suspension is used for magnetic hyperthermia treatment and comprises about 20 mg/ml-200 mg/ml of the superparamagnetic particles.

11. A method of locating a lymph node in a patient, the method comprising the steps of:

providing the hypoosmotic suspension of claim 1;
injecting the hypoosmotic suspension into the patient;
waiting until the superparamagnetic particles become entrapped in a lymph node; and
detecting the location of the lymph node by detecting the location of the superparamagnetic particles.

12. A method of location a lymph node in a patient, the method comprising the step of:

providing the hypoosmotic suspension of claim 1;
providing a hypoosmotic suspension comprising superparamagnetic particles, injecting the hypoosmotic suspension into the patient; and detecting a lymph node within 5 minutes of injection by detection the location of the superparamagnetic particles, the detecting sufficient to immediately begin a medical procedure on the lymph node based on the detecting.

13. A method of treating a patient using magnetic hyperthermia, the method comprising the steps of:

providing the hypoosmotic suspension of claim 1;
injecting the hypoosmotic suspension into the patient; and
exposing the patient to an alternating magnetic field.

14. The hypoosmotic suspension of claim 1, wherein the inorganic salt is selected from the group consisting of sodium chloride, potassium chloride, magnesium chloride, ammonium chloride, sodium sulfate, sodium phosphate, potassium phosphate, calcium chloride, magnesium sulfate, potassium acetate, and sodium acetate.

* * * * *